(12) United States Patent
Dussaud et al.

(10) Patent No.: US 9,243,142 B2
(45) Date of Patent: Jan. 26, 2016

(54) ASSOCIATION PRODUCT OF AMINO FUNCTIONAL HYDROPHOBIC POLYMERS WITH HYDROPHILIC POLYMERS CONTAINING ACID GROUPS, METHODS OF PREPARATION, AND APPLICATIONS FOR EMPLOYING THE SAME

(75) Inventors: Anne Dussaud, Tarrytown, NY (US);
Ning Lu, Chappaqua, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 504 days.

(21) Appl. No.: 13/297,926

(22) Filed: Nov. 16, 2011

(65) Prior Publication Data
US 2013/0121948 A1    May 16, 2013

(51) Int. Cl.
| | |
|---|---|
| *A61K 8/898* | (2006.01) |
| *A61K 8/90* | (2006.01) |
| *C08K 5/01* | (2006.01) |
| *C08K 5/101* | (2006.01) |
| *C08L 53/00* | (2006.01) |
| *C08L 79/02* | (2006.01) |
| *C08L 71/02* | (2006.01) |
| *C08L 83/08* | (2006.01) |
| *C08L 83/12* | (2006.01) |
| *A61Q 5/12* | (2006.01) |
| *A61K 8/37* | (2006.01) |
| *A61K 8/81* | (2006.01) |
| *A61K 8/04* | (2006.01) |

(52) U.S. Cl.
CPC ................ *C08L 79/02* (2013.01); *A61K 8/042* (2013.01); *A61K 8/37* (2013.01); *A61K 8/8152* (2013.01); *A61K 8/898* (2013.01); *A61Q 5/12* (2013.01); *C08L 71/02* (2013.01); *C08L 83/08* (2013.01); *C08L 83/12* (2013.01); *A61K 2800/48* (2013.01); *A61K 2800/594* (2013.01); *C08G 2650/50* (2013.01)

(58) Field of Classification Search
CPC ......... C08L 79/02; C08L 83/08; C08L 83/12; C08L 33/02
USPC ........... 424/70.12, 70.122; 508/204; 523/425; 524/313
See application file for complete search history.

(56) References Cited

U.S. PATENT DOCUMENTS

| | | | |
|---|---|---|---|
| 3,654,370 A | 4/1972 | Yeakey | |
| 3,915,921 A | 10/1975 | Schlatzer, Jr. | |
| 4,692,502 A | 9/1987 | Uebele et al. | |
| 5,288,814 A | 2/1994 | Long, II et al. | |
| 5,468,797 A | 11/1995 | Adams et al. | |
| 5,641,890 A | 6/1997 | Westley et al. | |
| 5,807,956 A | 9/1998 | Czech | |
| 6,475,568 B1 | 11/2002 | Czech | |
| 7,151,137 B2 | 12/2006 | Morschhauser et al. | |
| 7,462,585 B2 * | 12/2008 | Uehara | 510/123 |
| 7,504,094 B2 | 3/2009 | Decoster et al. | |
| 7,722,859 B2 | 5/2010 | L'Alloret | |
| 7,851,548 B2 | 12/2010 | Anyanwu et al. | |
| 2008/0312343 A1 | 12/2008 | Braun et al. | |
| 2009/0274643 A1 | 11/2009 | Anyanwu et al. | |

FOREIGN PATENT DOCUMENTS

| | | |
|---|---|---|
| CA | 2209060 | 1/2007 |
| DE | 10 2007 009 647 | 8/2008 |
| EP | 0816403 B1 | 5/2004 |
| JP | 2009/209123 | 9/2009 |
| WO | WO 2004/041986 A1 | 5/2004 |
| WO | 2012/120043 | 9/2012 |

OTHER PUBLICATIONS

Wagner et al. (Applied Organometallic Chemistry, vol. 10, pp. 421-435, Published 1996).*
Grunlan et al. (Polymer, pp. 2517-2523, Published 2004).*
International Search Report dated Apr. 3, 2013.
U.S. Appl. No. 13/297,931, filed Nov. 16, 2011 (claims enclosed).
Reversible Thermothickening of Aqueous Polymer Solutions; Hourdet et al., received Jun. 16, 1993; Polymer vol. 35, No. 12; pp. 2624-2630 (1994).
Synthesis of Thermoassociative Copolymers; Hourdet D., et al., Polymer, vol. 38, No. 10, pp. 2535-2547 (1997).
Poly(alkylene Oxides) and Polymeric Poly(carboxylic Acids); Smith et al., Industrial and Engineering Chemistry, vol. 51, No. 11; pp. 1361-1364 (1959).

* cited by examiner

*Primary Examiner* — Alma Pipic
(74) *Attorney, Agent, or Firm* — Dominick G. Vicari; Joseph S. Ostroff

(57) ABSTRACT

There is provided herein a composition comprising the non-covalent bonded reaction product of a hydrophilic polymer containing an acid functional group and a hydrophobic polymer which contains an amine group bound directly to the hydrophobic polymer backbone; and, optionally a diluent, as well as a process of making such a composition.

12 Claims, 1 Drawing Sheet

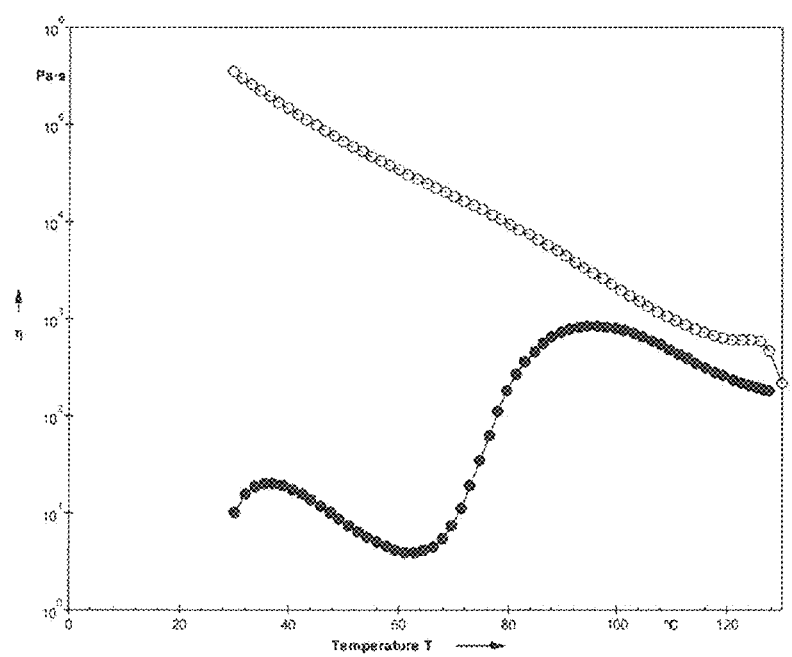
Thermothickening example obtained with a composition containing 44.5% copolymer 4, 44.5% isopropylmyristate, 11% carbopol 1382 (example 7, table 2). Bold symbols represent the heating curve, hollow symbols represent the cooling curve.

US 9,243,142 B2

ASSOCIATION PRODUCT OF AMINO FUNCTIONAL HYDROPHOBIC POLYMERS WITH HYDROPHILIC POLYMERS CONTAINING ACID GROUPS, METHODS OF PREPARATION, AND APPLICATIONS FOR EMPLOYING THE SAME

This application incorporates by reference the entire contents of the application entitled BLOCK ABA SILICONE POLYALKYLENEOXIDE COPOLYMERS, METHODS OF PREPARATION, AND APPLICATIONS FOR EMPLOYING THE SAME, filed on Nov. 16, 2011, which has the same inventors and assignee as herein.

The present invention relates to a non-covalently bonded reaction product of a hydrophobic polymer and a hydrophilic polymer containing an acid group.

BACKGROUND OF THE INVENTION

In addition to its thickening power in a particular solvent, a thickener may need to meet a broad range of requirements depending on the application. For example, a thickener may need to have a particular shear thinning behavior, low tack on drying, emulsifying property, or a particular thickening profile at elevated temperature.

Acrylate-based thickeners and other acid containing polymers derived from olefinically unsaturated polymerisable monomers have been tailored to cover a broad range of applications involving aqueous systems.

Hair care rinse-off products are commonly used to condition hair and improve hair combability because such products are convenient to use and leave hair with a clean feel. However, only a small amount of the conditioning agent is deposited on the hair and most of the conditioning agent is washed off and lost down the drain. With increasing environmental concern on sewer water pollution, leave-on conditioners that can be applied on damp hair, while leaving hair with a clean feel would be very beneficial.

Shine or luster is a very desirable hair attribute for all hair types and hair conditions. Silicones are among the most efficient shine agents. In most common shine-enhancing hair products, silicones are dissolved in a solvent and the products are applied as a spray or a non-aqueous gel. Typically those products are applied on dry hair and a much higher dose of silicones is deposited on the hair, therefore providing better shine than a rinse-off product. However, these products tend to leave an oily finish on the hair and their conditioning effects are usually poor. Moreover, the large use of volatile solvent in these product forms is also a disadvantage.

Therefore, it would be desirable to have a thickened aqueous system that provides conditioning, shine-enhancement and clean after-feel at the same time.

SUMMARY OF THE INVENTION

The inventors herein have unexpectedly discovered, that the physical association of acid containing aqueous thickeners with a hydrophobic polymer containing at least one amine group can thicken an oil phase. The thickening of the oil phase occurs upon heating and is irreversible. The non-covalently bonded reaction product ("the association product") can also readily swell in water, displaying enhanced thickening, emulsifying and sensory properties compared to acrylate based thickener alone. The low tack of the final aqueous emulsion is particularly useful in personal care applications, especially for hair and skin conditioning.

There is provided herein a composition comprising the non-covalent bonded reaction product of a hydrophilic polymer containing an acid functional group and a hydrophobic polymer which contains an amine group bound directly to the hydrophobic polymer backbone which does not contain an ethylene oxide moiety or contains an ethylene oxide moiety to propylene oxide moiety ratio of less than 3; and, optionally a diluent.

The present invention is further described in the detailed description section provided below.

DETAILED DESCRIPTION OF THE INVENTION

It has been unexpectedly discovered by the inventors herein:

(i) that the non-covalently bonded reaction product of crosslinked polyacrylic polymers with amino silicone copolymers of a specific structure can thicken low polarity fluids, such as ester, mineral oil, triglyceride oils and low viscosity silicone oils;

(ii) that the non-covalently bonded reaction product of crosslinked polyacrylic polymers with an amino silicone copolymer with certain amine/acid ratios swells immediately in water upon neutralization and can significantly enhance the thickening of aqueous systems compared to the crosslinked polyacrylic polymers alone;

(iii) that the non-covalently bonded reaction product of crosslinked polyacrylic polymers with an amino silicone copolymer of structure with certain amine/acid ratios help emulsify and stabilize organic and silicone oils and mineral oils in aqueous emulsions;

(iv) that the non-covalently bonded reaction product can provide both conditioning and thickening benefits for personal care products and cosmetics; and, (iv) that the non-covalently bonded reaction product of the present invention is useful in industrial applications involving thickening of aqueous phase such as the textile industry, oil extraction, coating, paints, agriculture, or in applications involving thickening of oil phase such as lubrication, emulsification and oil extraction.

In particular, thermothickening displayed by the non-covalently bonded reaction product of crosslinked polyacrylic acid with an amino silicone copolymer with certain structures can be useful in applications requiring irreversible thickening at high temperature, such as those described herein.

In the specification and claims herein, the following terms and expressions are to be understood as indicated.

As used in the specification and including the appended claims, the singular forms "a," "an," and "the" include the plural, and reference to a particular numerical value includes at least that particular value, unless the context clearly dictates otherwise.

Ranges expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising", "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "aliphatic hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

It will be understood herein that all measures of viscosity are obtained at 25 degrees Celsius unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Examples of useful monovalent hydrocarbon radicals for the silicones described herein include those independently selected from the group consisting of methyl, ethyl, n-propyl, iso-propyl, n-butyl, isobutyl, tert-butyl, n-pentyl, iso-pentyl, neopentyl, tert-pentyl, hexyl, such as the n-hexyl group, heptyl, such as the n-heptyl group, octyl, such as the n-octyl snf isooctyl groups, 2,2,4-trimethylpentyl, nonyl, such as the n-nonyl group, decyl, such as the n-decyl group, cycloalkyl radicals, such as cyclopentyl, cyclohexyl, cycloheptyl and methylcyclohexyl, and aryl groups such as phenyl, naphthyl; o-, m- and p-tolyl, xylyl, ethylphenyl, and benzyl.

A non-covalently bonded reaction product (an association product) between a hydrophilic polymer containing an acid functional group and a hydrophobic polymer which contains an amine group bound directly to the hydrophobic polymer backbone results from a non-covalent interaction(s), such as at least one ionic interaction(s) and/or at least one hydrogen bond(s). Formation of such a non-covalently bonded reaction product results in an increase in viscosity by at least one order of magnitude in anhydrous condition.

A hydrophobic polymer as used herein is a polymer that does not dissolve in water, and can dissolve in low polarity oils at concentration of at least 5% by weight.

A hydrophilic polymer as used herein is a polymer that can be solubilized, swelled or dispersed in water.

In one embodiment herein, the hydrophilic polymer containing an acid functional group is a polymer containing at least one acid functional group such as, for example, a carboxylic group, a sulfonic groups, or a phosphonic group. Those acid groups can be non-neutralized or partially neutralized in a salt form. The polymer can be linear, branched or crosslinked.

In one embodiment, suitable hydrophilic polymer containing an acid functional group are one or more selected from the group consisting of:

(I) polyacrylates polymers, such as homopolymers or copolymers containing acrylic acid monomers and optionally nonionic monomers or cationic monomers. The carboxylic acid containing polymers are prepared from monomers containing at least one activated >C=C< group and a carboxyl group. Such polymers are homopolymers of an unsaturated, polymerizable carboxylic monomers such as acrylic acid, methacrylic acid, maleic acid, itaconic acid, maleic anhydride, and the like, and copolymers of polymerizable carboxylic monomers with acrylate/methacrylate esters, acrylamides, olefins, vinyl esters, vinyl ethers, or styrenics. The carboxylic acid containing polymers have molecular weights greater than about 500 to as high as several million, usually greater than about 10,000 to 900,000 or more. The carboxylic monomers are the olefinically-unsaturated carboxylic acids containing at least one activated carbon-to-carbon olefinic double bond, and at least one carboxyl group. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides are useful herein. The preferred carboxylic monomers are the monoolefinic acrylic acids acrylic and methacrylic acid. Other useful carboxylic monomers are maleic acid and its anhydride. The polymers include both homopolymers of carboxylic acids or anhydrides thereof, or the defined carboxylic acids copolymerized with one or more other vinylidene monomers containing at least one terminal >$CH_2$ group. The hydrophilic polymers also may be the kinds which are cross-linked with any polyene, e.g. decadiene or trivinyl cyclohexane; acrylamides, such as methylene bis acrylamide; polyfunctional acrylates, such as trimethylol propane triacrylate; or polyfunctional vinylidene monomer containing at least 2 terminal $CH_2<$ groups, including for example, butadiene, isoprene, divinyl benzene, divinyl naphthlene, allyl acrylates and the like. Some such suitable crosslinked commercial polyacrylic polymers are carbopols such as carbopol 980, carbopol 1382, Ultrez 10 available from Lubrizol. Examples of suitable polymers are described in U.S. Pat. No. 3,915,921 and U.S. Pat. No. 5,468,797 the contents of which are incorporated by reference herein;

(II) homopolymers or copolymers containing monomers containing sulfonic groups such as MAPS (2-acrylamido-2-methylpropanesulfonate) and optionally containing nonionic monomers or cationic monomers. Some such homopolymers or copolymers are those containing inorganic acid moieties and their salts and esters. Preferred acids are vinylphosphonic acid, vinylsulfonic acid, allylphosphonic acid, and methallylsulfonic acid and allyl esters of phosphoric acid; and/or vinylphosphonic acid derivatives. The acid function of the monomers is especially the sulfonic acid function or the phosphonic acid function. Said monomers are, for example, partially or totally salified styrenesulfonic acid or, preferably, partially or totally salified 2-methyl-2-[(1-oxo-2-propenyl) amino]-1-propanesulfonic acid (also known as 2-acrylamido-2-methylpropane-sulfonic acid). Some such suitable commercial polymers are Sepigel 305 from Seppic, Aristoflex AVC from Clariant. Examples of suitable polymers are described in European Patent No. 0816403B1, U.S. Pat. No. 7,151,137 and U.S. Patent Application Publication No. 20080312343, the contents of each of which are incorporated by reference herein;

(III) polysaccharides containing acidic groups such as carboxymethylated starch, potato starch, carboxylmethylated cellulose, pectins, xanthan gums and the like; and, In one embodiment, hydrophilic polymer containing an acid functional group can be in bulk form, a dispersion or an emulsion.

In one other embodiment, the hydrophobic polymer which contains an amine ("amino") group bound directly to the hydrophobic polymer backbone can be a silicone polymer, specifically an amino silicone. In one specific embodiment, the hydrophobic polymer which contains an amine group bound directly to the hydrophobic polymer backbone can contain hydrophobic segments such as propylene oxide, siloxanes, alkyl groups, or a combination of such groups. Specifically, the amine content of the hydrophobic polymer which contains an amine group bound directly to the hydrophobic polymer backbone is from about 0.05 meq/g to about 5 meq/g, specifically from about 0.07 to about 1 meq/g and most specifically from about 0.1 to about 0.6 meq/g.

Suitable hydrophobic polymer which contains an amine group bound directly to the hydrophobic polymer backbone can be at least one selected from the group consisting of:

(i) Polyether amines based on propylene oxide. Suitable polyether amines include monamines and diamines having a molecular weight of from about 150 to about 12,000. The polyether amines used in the practice of this invention can be prepared using well known amination techniques such as described in U.S. Pat. No. 3,654,370. Generally, the polyether amines are made by aminating a polyol, such as a polyether polyol with ammonia in the presence of a catalyst such as a nickel containing catalyst such as a Ni/Cu/Cr catalyst. Suitable polyether blocks for the polyether amine include, polypropylene glycol, poly(1,2-butylene glycol), and poly (tetramethylene glycol). Generally, the glycols are prepared from ethylene oxide, propylene oxide or combination thereof using well known methods such as by a methoxy or hydroxy initiated reaction. Suitable commercial polymers are for example Jeffamine D230, D400, D2000, D4000. The present inventors herein have unexpectedly discovered that if the polyether amine (i) has a EO/PO ratio >3, it does not form a stable mixture with the hydrophilic polymer and the low polarity diluent, therefore it cannot thicken an oil phase.

(ii) linear amino silicone copolymers resulting from the reaction of $R^1NH_2$ and

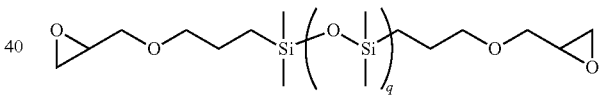

wherein q is from 1 to about 1000, specifically from about 10 to about 500; and,

where $R^3$=H or
where $R^3$=($C_nH_{2n-1}$)— where n is an integer of from 1 to 30; or where $R^3$=($C_nH_{2n-1}$)— where n is an integer of from 2 to about 30;
or where $R^3$=($C_nH_{2n-3}$)— where n is an integer of from 4 to 30; and,
m=0 or an integer of from 1 to 200, a is an integer of from 2 to 4.

(iii) amino silicone copolymers with [AB]$_n$ structure, such as for example, a non-hydrolyzable, random block polysiloxane, polyalkyleneoxide copolymer linked by a bis-amino-functional group, which on one end forms a tertiary amine linkage between the monomers within the polymer chain and the other end resides as a pendant aminofunctional group. One example of such is a non-hydrolyzable, random blocked polysiloxane-polyalkylene oxide composition having the Formula (I):

wherein each A is independently a polysiloxane unit of structure —$CR^1R^2$—$CR^3(OH)R^5$—$(SiR^4_2O)_x$—$SiR^4_2$—$R^5CR^3$ (OH)CR$^1$R$^2$-L- wherein each R$^1$ is selected independently from the group consisting of a hydrogen, and an alkyl, aryl, alkenyl, and aralkyl containing from 1 to 20 carbon atoms and optionally contains an oxygen atom; each R$^2$ is selected independently from the group consisting of a hydrogen, a chemical bond between the carbon atom and a different carbon atom of R$^3$ to form a ring structure, an alkyl, aryl, alkenyl, and aralkyl containing from 1 to 20 carbon atoms and optionally contains an oxygen atom; each R$^3$ is selected independently from the group consisting of a hydrogen, an alkyl, aryl, alkenyl, and aralkyl containing from 1 to 20 carbon atoms and optionally contains an oxygen atom, with the proviso that if R$^2$ is a chemical bond, then R$^3$ is a divalent hydrocarbon of 1 to 20 carbon atoms an optionally contains an oxygen atom that form a ring containing the chemical bond, R$^2$; each R$^4$ is independently selected from the group consisting of hydrogen, and an alkyl, alkenyl, aryl or aralkyl group containing 1 to 10 carbon atoms; each R$^5$ is a divalent hydrocarbon radical containing from 1 to 20 carbon atoms and optionally containing an oxygen atom; each L is independently a divalent linking group selected from the group consisting of

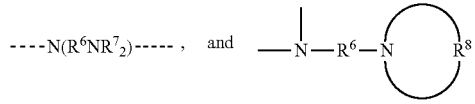

wherein each R$^6$ is a divalent hydrocarbon radical containing from 1 to 20 carbon atom, each R$^7$ is an independently monovalent hydrocarbon radical containing from 1 to 20 carbon atoms and R$^8$ is a divalent hydrocarbon of containing 2 to 20 carbon atoms and optionally contains an oxygen atom or an —NR$^7$— group; and x is an integer from 1 to 500; each B is independently a polyalkylene oxide unit of structure —CR$^1$R$^2$—CR$^3$(OH)R$^5$—O(C$_a$H$_{2a}$O)$_b$R$^5$C—R$^3$(OH) CR$^1$R$^2$-L- wherein each R$^1$ is selected independently from the group consisting of a hydrogen, and an alkyl, aryl, alkenyl, and aralkyl containing from 1 to 20 carbon atoms and optionally contain a oxygen atom; each R$^2$ is selected independently from the group consisting of a hydrogen, a chemical bond between the carbon atom and a different carbon atom of R$^3$ to form a ring structure, an alkyl, aryl, alkenyl, and aralkyl containing from 1 to 20 carbon atoms and optionally contain a oxygen atom; each R$^3$ is selected independently from the group consisting of a hydrogen, an alkyl, aryl, alkenyl, and aralkyl containing from 1 to 20 carbon atoms and optionally contain a oxygen atom, with the proviso that if R$^2$ is a chemical bond, then R$^3$ is a divalent hydrocarbon of 1 to 20 carbon atoms an optionally contains an oxygen atom that form a ring containing the chemical bond, R$^2$; each R$^5$ is a divalent hydrocarbon radical containing from 1 to 20 carbon atoms and optionally containing an oxygen atom; each L is independently a divalent linking group selected from the group consisting of

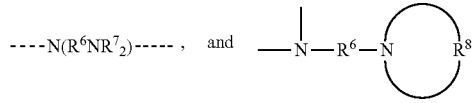

wherein each R$^6$ is a divalent hydrocarbon radical containing from 1 to 20 carbon atom, each R$^7$ is an independently monovalent hydrocarbon radical containing from 1 to 20 carbon atoms and R$^8$ is a divalent hydrocarbon of containing 2 to 20 carbon atoms and optionally contains an oxygen atom or an —NR$^7$— group; and x is an integer from 1 to 500; each E$^1$ is a monovalent end-group independently selected from the group consisting of,

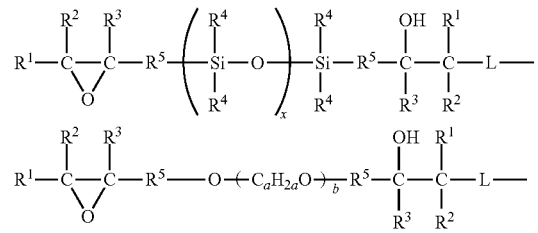

and H-L; and each E$^2$ is a monovalent end-group independently selected from the group consisting of hydrogen,

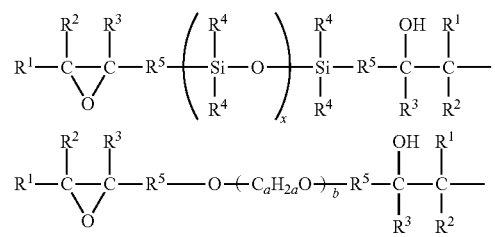

each m and n is independently an integer from 1 to 500, and a is from 2 to 4, b is from 2 to 100, and preferably 3 to 50 and where R$^1$, R$^2$, R$^3$, R$^4$ and R$^5$ are each independently as defined above.

One other example of (AB)$_n$A type copolymers (iii) which can be the hydrophobic polymer which contains an amine group directly bound to the hydrophobic polymer backbone described above can have in their structure polysiloxane units {XR$^2$[(SiO(R$^1$)$_2$]$_x$Si(R$^1$)$_2$R$^2$X}, polyalkyleneoxide units {YO(C$_a$H$_{2a}$O)$_b$Y} and linking groups —NR$^3$—, wherein R$^1$ is alkyl, R$^2$ is a divalent organic moiety, X and Y are divalent organic groups formed by the ring opening of an epoxide, R$^3$ is selected from the group consisting of alkyl, alkenyl, aryl, aralkyl, oxygen-containing alkyl, oxygen-containing aryl, and oxygen-containing aralkyl, a=2 to 4, b=2 to 100, preferably 3 to 50, x=1 to 500, preferably 150.

R$^1$ is preferably lower alkyl, e.g., an alkyl having from one to four carbon atoms, i.e., methyl, ethyl, propyl, butyl, and isomers of the foregoing, e.g., isopropyl, t-butyl, and the like. More preferably, R$^1$ is methyl.

R$^2$ is preferably a divalent hydrocarbon group with at least one carbon, which may have hydroxy substitutions thereon and/or include an ether linkage. Preferably, it contains less than ten carbon atoms. Within a particular molecule, each R$^1$, R$^2$, R$^3$ and R$^4$ may be the same or different.

The copolymers are preferably end-capped with secondary amino groups —NHR$^3$ or tertiary groups —NR$^3$R$^4$, where R$^3$ is as defined above for linking groups —NR$^3$— and R$^4$ is also chosen from the group consisting of alkyl, alkenyl, aryl, aralkyl, oxygen-containing alkyl, oxygen-containing aryl, and oxygen-containing aralkyl, and where R$^3$ and R$^4$ can be the same or different.

The moieties comprising R$^3$ and R$^4$ preferably comprise from one to about twenty carbon atoms, e.g., methyl, ethyl, propyl, butyl, pentyl, hexyl, heptyl, octyl, nonyl, decyl, undecyl, oleyl, dodecyl, tridecyl, tetradecyl, pentadecyl, hexadecyl, heptadecyl, octadecyl, nonadecyl, eicosyl, methoxy, ethoxy, propoxy, butoxy, phenyl, biphenyl, naphthyl, tolyl, xylyl, anthracyl, methoxyphenyl, isomers of the foregoing, and the like.

The copolymers are not (AB)n type because blocks may consist of more than one unit, therefore the nominal length of the blocks will vary. Moreover, blocks comprising more than one unit will be interrupted with the amino groups. The number of units per molecule is limited by the ability to handle high viscosity material, since the viscosity is directly proportional to the number of units, but practically there should be at least two of each unit and may be up to 1,000 units. It is preferred that the terminal groups of the copolymer be amino groups, as noted above.

The molecular weight of the copolymers can be modified by varying the molar ratio of the epoxy component to amino component, by varying the number of oxyalkylene units and the number of siloxy groups within the polysiloxane blocks.

The ring-opened epoxides, represented by either X or Y, may be aliphatic, cycloaliphatic, and may contain aromatic rings. They also contain hydroxy groups and may contain an ether linkage. Preferably, the ring-opened epoxide is chosen from the following: —CH$_2$CH(OH)(CH$_2$)$_v$CH(OH)CH$_2$—CH[CH$_2$OH](CH$_2$)$_v$CH[CH$_2$OH]—, —CH$_2$CH(OH)(CH$_2$)$_v$CH[CH$_2$OH]—, —(CH$_2$)$_v$—OCH$_2$CH(OH)CH$_2$—; —(CH$_2$)$_v$OCH$_2$CH(CH$_2$[OH])— with v=2 to 6. Alternatively, the ring-opened epoxides may be derived from the following epoxycyclohexyl alkylene groups, omega-(3,4-epoxycyclohexyl)alkylene, beta-(3,4-epoxycyclohexyl)ethylene, beta-(3,4-epoxycyclohexyl)-beta-methylethylene, and beta-(3,4-epoxy-4-methylcyclohexyl)-beta-methylethylene.

The polyoxyalkylene blocks represented by (C$_a$H$_{2a}$O) or (OC$_a$H$_{2a}$) may be made up of ethylene oxide (a=2), propylene oxide (a=3), and butylene oxide (a=4) in a random or blocked fashion. The molar ratio EO/PO content is preferably less than 3.

In one other embodiment one example of (AB)$_n$A type copolymers (iii) which can be the hydrophobic polymer which contains an amine group directly bound to the hydrophobic polymer backbone described above can be such as those described in U.S. Pat. No. 6,475,568 and U.S. Pat. No. 7,851,548 the contents of both of which are incorporated by reference herein.

Some examples of amino silicone copolymers with [AB]n structure (iii) can have alternating units of polysiloxane [X(C$_a$H$_{2a}$O)$_b$R$^2$[(SiO(R$^1$)$_2$]$_2$Si(R$^1$)$_2$R$^2$(OC$_a$H$_{2a}$)$_b$X] and polyalkyleneoxides [YO(C$_a$H$_{2a}$O)$_d$Y] wherein R$^1$ is a C1 to C4 alkyl, preferably methyl, R$^2$ is a divalent organic moiety, X and Y are divalent organic groups selected from a secondary or tertiary amine and a ring opened epoxide, such that when X is a ring opened epoxide, Y is an amine and vice versa, a is 2 to 4, preferably 2 to 3, each occurrence of b is 0 to 200, d is 0 to 100, (b+d) is 1 to 100, preferably 10 to 50, and c is 1 to 500, preferably 10 to 100. The total number of repeating units is limited only by the ability to handle high viscosity material, since the viscosity increases as does the number of units, but practically there should be at least two of each unit and may be up to 1,000 units. It is preferred that the unit containing the amine should be the terminal units of the copolymer, i.e., the A in (AB)$_n$A.

The ring opened epoxides, represented by either X or Y, may be aliphatic, cycloaliphatic, and may contain aromatic rings. They also contain hydroxy groups and may contain an ether linkage. Preferably the ring opened epoxide is chosen from the following:

—CH$_2$CH(OH)(CH$_2$)$_v$CH(OH)CH$_2$—CH[CH$_2$OH](CH$_2$)$_v$CH[CH$_2$OH]—, —CH$_2$CH(OH)(CH$_2$)$_v$CH[CH$_2$OH]—, —(CH$_2$)$_v$—OCH$_2$CH(OH)CH$_2$—, —(CH$_2$)$_v$OCH$_2$CH(CH$_2$[OH])— with v=2 to 6.

Alternatively, the ring opened epoxides may be derived from the following epoxycyclohexyl alkylene groups, omega-(3,4-epoxycyclohexyl)alkylene, beta-(3,4-epoxycyclohexyl)ethylene, beta-(3,4-epoxycyclohexyl)beta-methylethylene, and beta-(3,4-epoxy-4-methylcyclohexyl)-beta-methylethylene.

The amines, represented by either X or Y, are secondary or tertiary amines. More specifically, the amines may be of the type —R$^4$N(R$^3$)(R$^4$)$_g$—, where R$^3$ may be an alkyl group with 1 to 4 carbons or hydrogen, most preferably methyl, and R$^4$ is an alkylene, cycloaliphatic alkylene or an aralkylene group, which may include heteroatoms, though an alkylene of less than ten carbons is preferred, and g may be 0 or 1.

R$^2$ is a divalent hydrocarbon group with at least one carbon, which may have hydroxy substitutions thereon and/or include an ether linkage. It is preferred that it contain less than ten carbons. Within a particular (AB)$_n$A molecule each R$^1$, R$^2$, R$^3$ and R$^4$ may be the same or different.

The polyoxyalkylene blocks represented by (C$_a$H$_{2a}$O) or (OC$_a$H$_{2a}$) may be made up of ethylene oxide (a=2), propylene oxide (a=3) and butylene oxide (a=4) in a random or blocked fashion. The molar ratio EO/PO content is preferably less than 3.

The molecular weight of the copolymers can be modified by varying the molar ratio of the epoxy component to amino component, by varying the number of oxyalkylene units and the number of siloxy groups within the polysiloxane blocks. Although it is important to generate materials with high molecular weight because properties essential to the application, such as softness and durability, are dependent upon the molecular weight of the polymer, it is also essential to produce, non-crosslinked structures, i.e., only linear molecules.

Another important factor controlling the properties of the copolymers is relative silicone content in the molecule, i.e., the values of c, and (b+d). Higher silicone content copolymers are usually more hydrophobic, therefore less water soluble and impart better softness. A preferred ratio of c to (b+d) is 10:1 to 1:10, and most preferably 2:1.

The copolymers are terminated with hydrogen, when the terminal groups are ring opened epoxides. When the terminal groups are amines as described herein, the copolymers are terminated with primary or secondary amine groups.

A particularly preferred copolymer may be of the following formula (X):

HN(R$^3$)(C$_a$H$_{2a}$O)$_b$CH(CH$_3$)CH$_2$N(R$^3$)[CH$_2$CH(OH)(CH$_2$)$_3$(SiO(R$^1$)$_2$)$_c$Si(R)$_2$(CH$_2$)$_3$OCH$_2$—CH(OH)CH$_2$—N(R$^3$)(C$_a$H$_{2a}$O)$_b$CH$_2$CH(CH$_3$)N(R$^3$)]$_y$H  (X)

where "y" is at least two and may be as high as allowable within the art of manufacturing high viscosity compositions and thus may range from 2 to about 1,000, depending on the values of b and c in formula (I). Examples of [AB]n copolymers (iii) are described in U.S. Pat. No. 5,807,956.

Amino silicone copolymers with [AB]$_n$ structure, can have a random arrangement of block A and B (AABABBBABBA . . . ) or an alternating arrangement of block A and B (ABABABAB . . . ). These differences result from different synthetic routes.

(iv) Amino silicone copolymer with a (ABA) structure where B is the siloxane block, resulting from the reaction of:

R$^1$R$^2$NH where $R^1=R^3(OC_aH_{2a})_m-$ and where $R^3=(C_nH_{2n+1})-$ and where n is an integer of from 1 to 30, or where $R^3=(C_nH_{2n-1})-$ where n is an integer of from 2 to 30, or where $R^3=(C_nH_{2n-3})-$ where n is an integer of from 4 to about 30, and m=0 or an integer of from 1 to 200, and a is an integer of from 2 to 4, where $R^2=H$ or $R^4(OC_cH_{2c})_o-$ where $R^4=(C_qH_{2q+1})-$ where q is an integer of from 1 to 30 or, where $R^4=(C_qH_{2q-1})-$ where q is an integer of from 2 to about 30, or where $R^4=(C_qH_{2q-3})-$ with q is an integer of from 4 to 30, and o=0 or an integer of from 1 to 200 and, c is an integer of from 2 to 4; and,

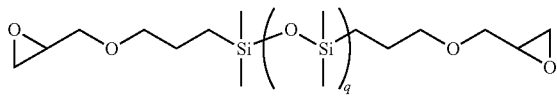

wherein q is and integer of from 2 to 1000, specifically 10 to 500.

(v) Amino terminated silicone

Amino terminated silicone is a silicone having at least one terminal amino functional group according to the formula: $R_{3-y}Q_ySiO[A]_xSiQ_zR_{3-z}$ wherein, A represents $R_2SiO$, wherein R is an alkyl group of 1 to 5 carbons, or a phenyl group, or an alkoxy group or a hydroxy group, Q, is an amine functional group of the formula $-R^2Z$, $R^2$, is a divalent alkylene radical of 3 to 6 carbons, preferably trimethylene, pentamethylene, $-CH_2CHCH_3CH_2-$, or $-CH_2CH_2CHCH_3CH_2-$, Z, is $-N(R^3)_2$ or $-NR^3(CH_2)_nN(R^3)_2$, $R^3$, is individually an H atom or alkyl group of 1 to 20 carbon atoms or phenyl or benzyl, and wherein: x is from 1 to 3000, y is from 0 to 3, z is from 1 to 3, n is from 2 to 6.

In one specific embodiment, R is an alkyl group of 1 to 5 carbons, or a phenyl group more specifically a methyl group, Q, is an amine functional group of the formula $-R^2Z$, $R^2$, is a divalent alkylene radical of 3 to 6 carbons, specifically trimethylene, pentamethylene, $-CH_2CHCH_3CH_2-$, or $-CH_2CH_2CHCH_3CH_2-$, more specifically a propyl or an isopropyl group, Z, is $-N(R^3)_2$ or $-NR^3(CH_2)_nN(R^3)_2$, more specifically $NH_2$ or $NHCH_2CH_2NH_2$, $R^3$, is individually an H atom or alkyl group of 1 to 20 carbon atoms or phenyl or benzyl, and wherein: x, is from 1 to 3000, more preferably is from 10 to 400, even more preferably from 70 to 200 and y is from 0 to 3, more preferably from 0 to 1, z is from 1 to 3, more preferably 1 and n is from 2 to 6.

In one other embodiment herein the composition described herein is other than a fabric treatment composition.

In one embodiment there is provided a hair care or skin care application comprising the composition described herein.

In one further embodiment there is provided a process of making a composition comprising non-covalently reacting a hydrophilic polymer containing an acid functional group; a hydrophobic polymer which contains an amine group bound directly to the hydrophobic polymer backbone; and, optionally a diluent.

In one embodiment there is provided a personal care application comprising a composition made by the process described herein.

In one further embodiment there is provided a hair care or skin care application comprising a composition made by the process described herein.

In one embodiment herein the optional diluents used herein can be low polarity oils and/or water. Low polarity oils need to be miscible with the hydrophobic polymer which contains an amine group bound directly to the hydrophobic polymer backbone and has a Hansen solubility parameter of from about 12 Mpa ½ to about 28 Mpa ½, specifically from about 14 to about 20 Mpa ½. Suitable oils include but are not limited to esters, mineral oils, silicone oils, triglycerides oils, fatty acids or combination of oils. Water can contain at least one inorganic or organic base such as ammonium hydroxide, sodium hydroxide, 2-amino-2-methyl-1-propanol (AMP-95), triethanolamine and the like.

Methods of Preparation (a) Method of Preparation in Anhydrous Condition

In a non-aqueous medium, the association product can be formed by blending the herein described hydrophilic polymer containing an acid functional group and the hydrophobic amino containing polymer (or any of the hydrophobic polymer which contains an amine group bound directly to the hydrophobic polymer backbone which is described herein) with optionally the herein non-aqueous diluent and heating the blend to above the effective glass transition temperature of the hydrophilic polymer containing an acid functional group, typically to 30° C. to 200° C., specifically from about 50° C. to about 150° Celsius, for a period of from about 1 min to about 120 min, followed by cooling the blend to room temperature. A significant increase of viscosity is observed. Typically, viscosity increases by at least one order of magnitude or more, specifically at least 1 order of magnitude. FIG. 1 shows a typical example of this thermo-thickening process. Alternatively, the blend can be left at room temperature and the viscosity increases will occur over a much longer time.

(b) Method of Preparation of Water-Swellable Association Products

A concentrate is prepared according to method (a), wherein the molar ratio of amine/acid is between 0.01-0.2, specifically between 0.03 and 0.1. Then an aqueous base solution is added at room temperature or at elevated temperature of from about 30° C. to about 95° C., specifically from about 40° C. to about 85° C. over a period of from about 5 min to about 120 min. In one specific embodiment there is use of a base such as 2-amino-2-methyl-1-propanol (AMP) or any of those described herein. In one embodiment, the hydrophilic polymer containing an acid functional group and a hydrophobic polymer which contains an amine group bound directly to the hydrophobic polymer backbone are present in an amount such that there is an molar amine/acid ratio of from about 1:20 to about 2:1, specifically from about 1:10 to about 1:1 and most specifically from about 1:8 to about 2:3.

(c) Method of Preparation in Aqueous Condition

The herein described hydrophilic polymer containing an acid functional group is mixed with water at a concentration of about 0.1% to about 20% at room temperature or elevated temperature from about 30° C. to about 95° C. If the herein described hydrophilic polymer containing an acid functional group is not already neutralized, an aqueous base solution is added to neutralize the aqueous system. Mixing should last for a period of about 5 min to about 120 min. The hydrophobic polymer which contains an amine group bound directly to the hydrophobic polymer backbone which is described herein) is blended with the low polarity herein described diluent(s) for a period of about 10 min to about 120 min, and then added to the neutralized aqueous dispersion of the herein described hydrophilic polymer containing an acid functional group. The mixing is performed with conventional mixing tools (shear blade, ross mixer etc.) for a period of about 30 min or more. More water is added to the blend, if necessary.

EXAMPLES

The examples below are provided for the purpose of illustrating the present invention. Examples 1-7 are part of the invention.

Example 1

Anhydrous Association Products (Method a)

The hydrophobic polymer containing at least one amine group used in this example is described in table 1.

The association products were prepared according to method (a), using a heating/cooling process. In examples 1-19 and 21-24 (Table 2), hydrophobic polymer containing at least one amine group was blended with a herein described low polarity diluent (either isopropylmyristate, mineral oil, polydimethylsiloxane, capric/caprylic triglyceride, or sunflower oil). The hydrophilic polymer containing an acid functional group [polyacrylate type (I) with the common name carbopol] was blended with the hydrophobic polymer/diluent blend in a Flakteck speedmixer at room temperature for a period of 3 min.

In example 20, the hydrophobic polymer was blended with the hydrophilic polymer without the use of a diluent in a Flakteck speedmixer for a period of 3 min. A small sample of the suspension of the hydrophobic polymer, hydrophilic polymer and diluent, if present, was placed on a parallel plate rheometer equipped with a Peltier temperature control unit. The viscosity of the sample was monitored at a constant shear rate of 0.05/s while the sample was heated from 30° C. to 130° C. at 2 degree/min, on the rheometer. After the sample had reached 130° C., the sample was cooled in the rheometer with a 2 degree/min cooling rate.

A typical viscosity curve as function of temperature corresponding to example 7 in table 2 is shown FIG. 1. It shows the very significant viscosity increase of the sample when temperature reached the vicinity of 80° C. Upon cooling, viscosity increased further. This irreversible thermothickening was observed with various hydrophobic polymers of the present description. In Table 2, the initial viscosities of various compositions of the present disclosure are shown and the final viscosity obtained after the heat/cool process. For the comparative examples 1 and 2, the use of silicone polyether copolymers (L8620, L7510), respectively, which do not contain amine groups, did not show a thermothickening behavior. In Comparative example 3, the aminosilicone Magnasoft Plus with pendant amine groups did not show a thermothickening effect either.

POLYMER A=hydrophobic polymer containing at least one amine group.

POLYMER B=hydrophilic polymer containing acid groups.

TABLE 1

Description of copolymers

| | Structure | Amine | Polyether (EO) | Polyether (PO) | Ratio EO/PO | q | Charge of epoxy terminated polysiloxane (g) | Charge of amine (g) |
|---|---|---|---|---|---|---|---|---|
| copolymer 1 | (ii) | ethanolamine | 0 | 0 | NA | 100 | 100 | 1.09 |
| copolymer 2 | (iii) | Jeffamine D-1000 | 0 | 33 | 0 | 100 | 61.45 | 18.00 |
| copolymer 3 | (iii) | oleylamine | 0 | 9 | 0 | 100 | 37.5 | 7.10 |
| copolymer 4 | (iv) | Jeffamine M-2005 | 6 | 29 | 0.2 | 100 | 413.90 | 250.00 |
| copolymer 5 | (iv) | Jeffamine M-2005 | 6 | 29 | 0.2 | 50 | 37.65 | 40.00 |
| copolymer 6 | (iv) | Jeffamine M-2005 | 6 | 29 | 0.2 | 380 | 274.29 | 40.00 |
| copolymer 7 | (iv) | Jeffamine M-600 | 1 | 9 | 0.1 | 100 | 67.14 | 11.00 |
| copolymer 8 | (iv) | Jeffamine M-600 | 1 | 9 | 0.1 | 50 | 62.47 | 18.00 |
| Polyetheramine 2 | | Jeffamine D4000 | 0 | 68 | | | | |
| Polyetheramine 3 | | Jeffamine D400 | 0 | 6.1 | | | | |
| comparative 1 | linear | | | | | | | |
| comparative 2 | comb | | | | | | | |
| comparative 3 | | | | | | | | |

(g) = grams,
(EO) = ethylene oxide moieties,
(PO) = propylene oxide moieties

The average number of repeat units of dimethylsiloxane in the silicone block (q) is shown in column 7 (for copolymer 1 the q corresponds to q in the epoxysilicone formula for (iii), for copolymer 3, q corresponds to x in the formula (I), for copolymers 2, q corresponds to c in formula X, for copolymers 4-8 q corresponds to q in the epoxysilicone formula for (iv)). The amine type used in the synthesis of the copolymer is shown in column 3. The average number of ethylene oxide and propylene oxide in the polyether block is shown in column 4 and 5 respectively. Polyetheramines 2 and 3 are commercial Jeffamines available from Huntsman.

Comparative Examples 1 and 2 employed silicone polyether copolymers which did not contain amine groups. Comparative Example 3 employed an aminosilicone containing secondary and tertiary pendant amine groups. Comparative example 1 L8620 is a linear silicone polyether block copolymer which does not contain amine group, and is commercial grade from Momentive. Comparative example 2 L7510 is a random comb silicone polyether copolymer which does not contain amine and is a commercial grade from Momentive. Comparative example 3 (Magnasoft plus) is a aminosilicone with pendant amine groups which is a commercial grade from Momentive.

Preparation Method of Copolymer 1

To a four-necked round-bottomed flask fitted with a mechanical stirrer, a condenser fitted with a nitrogen inlet, a thermocouple and an additional funnel was charged with 100.00 gram of the epoxy-terminated polysiloxane [$CH_2(O)CHCH_2$—O—$(CH_2)_3Si(CH_3)_2[OSi(CH_3))_2]_{100}OSi(Me_2)(CH_2)_3OCH_2CH(O)CH_2$], 1.09 gram of ethanolamine, 32.19 g isopropanol, and 100 ppm of Vitamin E. The contents of the flask were heated with stirring to 80° C. until all the epoxy groups were reacted. This typically required 10 hours. The reaction was deemed complete when all the epoxy functionality, determined by titration, was consumed.

Preparation Method of Copolymer 3

To a four-necked round-bottomed flask fitted with a mechanical stirrer, a condenser fitting with a nitrogen inlet, a thermocouple and an additional funnel, was charged with 37.50 g of the epoxy-terminated polysiloxane [$CH_2(O)CHCH_2$—O—$(CH_2)_3Si(CH_3)_2[OSi(CH_3))_2]_{100}OSi(Me_2)(CH_2)_3OCH_2CH(O)CH_2$], 7.10 g of oleylamine, 61.22 g isopropanol, and 100 ppm of Vitamin E. The contents of the flask were heated with stirring to 80° C. for two hours, after which 3.58 g of an epoxy-ended blocked polyalkyleneoxide (DER 732 commercially available from Dow Chemical) was added to the flask. After two hours of heating, another portion of the epoxy-terminated polysiloxane DER 732 (37.50 g) was added to the flask. After two hours of heating, 3.58 g of DER 732 was added. The reaction mixture was maintained at 80° C. until all the epoxy groups were reacted. This typically required 10 hours. The reaction was deemed complete when all the epoxy functionality, determined by titration, was consumed.

Preparation Method of Copolymer 2 and 4 to 8

The amino-functionalized polymer and a sufficient amount of isopropanol to make a 50% of solution of the final copolymer were charged in a four-neck flask equipped with a stirrer, addition funnel, reflux condenser and thermocouple. The temperature of the reaction mixture was adjusted to 80° C. and an epoxy-terminated polysiloxane [$CH_2(O)CHCH_2$—O—$(CH_2)_3Si(CH_3)_2[OSi(CH_3))_2]_qOSi(Me_2)(CH_2)_3OCH_2CH(O)CH_2$] (charges and the value of q provided in Table 1) was added from an addition funnel. The reaction was completed when the epoxy functionality, determined by titration, was consumed. This typically required 6 to 10 hours.

TABLE 2

Anhydrous Composition and thermo-thickening results

| Example | Polymer (A) | Conc. A wt. % | Polymer (B) | Conc. B wt. % | Diluent (C) | Conc. C wt % | amine/acid | Initial viscosity (Pa · s) at 30° C. | Viscosity (Pa · s) after heat/cool at 30° C. |
|---|---|---|---|---|---|---|---|---|---|
| 1 | copolymer 1 | 72 | Carbopol 1382 | 10 | isopropylmyristate | 18 | 0.07 | 229 | 126,000 |
| 2 | copolymer 1 | 63 | Carbopol 1382 | 5.5 | light mineral oil | 31.5 | 0.12 | 104 | 69,000 |
| 3 | copolymer 1 | 49.5 | Carbopol 1382 | 1 | isopropylmyristate | 49.5 | 0.51 | 70 | 7,330 |
| 4 | copolymer 2 | 44.5 | Carbopol Ultrez20 | 11 | isopropylmyristate | 44.5 | 0.08 | 46 | 34,600,000 |
| 5 | copolymer 2 | 49.5 | Carbopol 1382 | 1 | isopropylmyristate | 49.5 | 0.99 | 70 | 71,800 |
| 6 | copolymer 3 | 48.5 | Carbopol 1382 | 3 | isopropylmyristate | 48.5 | 0.40 | 88 | 10,600 |
| 7 | copolymer 4 | 44.5 | Carbopol 1382 | 11 | isopropylmyristate | 44.5 | 0.06 | 65 | 348,000 |
| 8 | copolymer 4 | 47.5 | Carbopol 1382 | 5 | isopropylmyristate | 47.5 | 0.13 | 45 | 52,500 |
| 9 | copolymer 4 | 48.5 | Carbopol 1382 | 3 | isopropylmyristate | 48.5 | 0.22 | 60 | 12,800 |
| 10 | copolymer 4 | 49.5 | Carbopol 1382 | 1 | isopropylmyristate | 49.5 | 0.67 | 197 | 2,550 |
| 11 | copolymer 5 | 44.5 | Carbopol 1382 | 11 | isopropylmyristate | 44.5 | 0.07 | 65 | 520,000 |
| 12 | copolymer 5 | 44.5 | Carbopol 1382 | 11 | polymethylsiloxane | 44.5 | 0.07 | 1.7 | 45,400 |
| 13 | copolymer 5 | 44.5 | Carbopol 1382 | 11 | capric/caprylic triglyceride | 44.5 | 0.07 | 225 | 29,300 |
| 14 | copolymer 5 | 44.5 | Carbopol 1382 | 11 | sunflower oil | 44.5 | 0.07 | 63 | 700 |
| 15 | copolymer 5 | 48.15 | Carbopol 1382 | 3.7 | isopropylmyristate | 48.15 | 0.24 | 16.6 | 44,800 |
| 16 | copolymer 5 | 49.5 | Carbopol 1382 | 1 | isopropylmyristate | 49.5 | 0.91 | 1.7 | 255 |
| 17 | copolymer 6 | 49.5 | Carbopol 1382 | 1 | isopropylmyristate | 49.5 | 0.28 | 10 | 48 |
| 18 | copolymer 7 | 44.5 | Carbopol 1382 | 11 | isopropylmyristate | 44.5 | 0.08 | 44 | 560,000 |
| 19 | copolymer 8 | 44.5 | Carbopol 1382 | 11 | isopropylmyristate | 44.5 | 0.13 | 56 | >10E6 |
| 20 | copolymer 8 | 95 | Carbopol 980 | 5 | none | 0 | 0.59 | 2800 | 581,000 |
| 21 | copolymer 2 | 45 | Luvimer 100P | 10 | i isopropylmyristate | 45 | — | 30 | 4,700 |
| 23 | Polyetheramine 2 | 44.2 | Carbopol 980 | 11.6 | isopropylmyristate | 44.2 | 0.30 | 517 | >10E6 |
| 24 | Polyetheramine 3 | 44.2 | Carbopol 1382 | 11.6 | isopropylmyristate | 44.2 | 1.42 | 531 | 293,000 |
| | Comparative 1 | 44.2 | Carbopol 1382 | 11 | isopropylmyristate | 44.2 | 0.06 | 593 | 270 |
| | Comparative 2 | 44.5 | Carbopol 1382 | 11 | isopropylmyristate | 44.5 | 0.00 | | 2 phases |
| | Comparative 3 | 44.5 | Carbopol 1382 | 11 | isopropylmyristate | 44.5 | 0.00 | | 2 phases |

The carbopols were commercial products from Lubrizol. Isopropylmyristate was from Kobo. The Polymer A's in Table 2 are those copolymers made as described above.

Luvimer 100 P is a terpolymer of tert.-butyl acrylate, ethylacrylate and methacrylic acid from BASF. Light mineral oil was from Pemreco. Capric caprylic triglyceride oil was from Alzo Int. Sunflower oil was from Welch, Holme & Clark Co. Polydimethylsiloxane had a viscosity of 5 cp and was from Momentive.

POLYMER A=hydrophobic polymer containing at least one amine group

POLYMER B=hydrophilic polymer containing acid groups.

Example 2

Water Swellable Association Products (Method b)

Example 2 demonstrated that the compositions of the invention form homogeneous stable concentrate pastes, which can swell upon the addition of alkaline water to form aqueous gels.

In this case, both the hydrophilic polymer containing an acid functional group (carbopols) and the hydrophobic polymer containing at least one amine group (copolymer 2 or copolymer 4) were added to the low polarity diluent (isopropylmyristate) before neutralization. In the comparative example, which contained oil (either isopropylmyristate or a mixture of isopropylmyristate and polydimethylsiloxane) and carbopol 1382 or carbopol Ultrez 20, the carbopol particles sedimented and the blend was unstable.

In example 25, copolymer 2, isopropylmyristate and carbopol Ultrez 20 were mixed in a Flaktech speed mixer for 2 min. Water was then added all at once and the mixture was blended in Flaktech speedmixer for 2 min. The sample was aged at 50° C., in an oven for 10 days. In examples 26 and 27, copolymer 4, isopropylmyristate and carbopol 1382 and carbopol 980 respectively were mixed with a conventional stirrer blade at 400 rpm at room temperature for 4 hours and aged overnight at 80° C. in an oven. Stability was evaluated visually after 2 months at room temperature.

TABLE 3

| | | example 25 | example 26 | example 27 | comparative 4 | comparative 5 |
|---|---|---|---|---|---|---|
| | | composition in wt % | | | | |
| copolymer 2 | Hydrophobic polymer | 43 | | | | |
| copolymer 4 | Hydrophobic polymer | | 44 | 44 | | |
| isopropylmyristate | Diluent | 43 | 44 | 44 | 90 | 44 |
| viscasil 60M | | | | | | 44 |
| carbopol Ultrez 20 | Hydrophilic polymer | 11 | | | | |
| carbopol 1382 | Hydrophilic polymer | | 12 | | 10 | 12 |
| carbopol 980 | Hydrophilic polymer | | | 12 | | |
| water | Diluent | 3 | 0 | 0 | 0 | 0 |
| texture | | paste | paste | paste | liquid | liquid |
| stability | | stable | stable | stable | unstable | unstable |

Copolymers 2 and 4 are described above.
Viscasil 60 M is a polydimethylsiloxane from Momentive.
The carbopols are from Lubrizol.
The copolymers 2 and 4 in Table 3 are those made as described above.

Association Product Thickening in Aqueous Emulsions

Table 4a-c demonstrates the thickening of emulsions formed by dilution with alkaline water of the concentrate paste composition shown in Table 3.

All the emulsions of the present invention have a higher viscosity than the gel thickened by the anionic thickener only (comparatives), at fixed concentration of thickener.

TABLE 4-a

Emulsion composition in wt % prepared from Example 25 (Table 3)

| | Example 28 | Comparative 6 | Example 29 | Comparative 7 | Example 30 | Comparative 8 |
|---|---|---|---|---|---|---|
| Copolymer 2 | 1.2 | | 2 | | 4 | |
| IPM | 1.2 | | 2 | | 4 | |
| Ultrez 20 | 0.3 | 0.3 | 0.5 | 0.5 | 1 | 1 |
| water | 97.3 | 99.7 | 95.5 | 99.5 | 91 | 99 |
| AMP | q.s to pH = 6 | q.s to pH = 6 | q.s to pH = 6 | q.s to pH = 6 | q.s to pH = 6 | q.s to pH = 6 |
| Viscosity (cp) | 55500 | 14500 | 110000 | 32000 | 196500 | 76000 | q.s. abbreviation means "as much as suffices"
IPM was isopropylmyristate from Alzo.
Ultrez 20 was a carbopol from Lubrizol.
Copolymers 2, is described above.
AMP is aminomethylpropapanol from Dow.

Example 28-30 were prepared by diluting the paste example 25 with a 9.5% solution of aminomethylpropanol (AMP) and water to adjust pH to about 6. Comparative Examples 6, 7 and 8 were prepared by dispersing the carbopol in water and neutralizing the system to pH=6 with aminomethylpropanol.

TABLE 4-b

Emulsion composition in wt % prepared from Example 27 (Table 3)

|  | Example 31 | Comparative 9 | Example 32 | Comparative 10 | Example 33 | Comparative 11 |
|---|---|---|---|---|---|---|
| Copolymer 4 | 1.1 |  | 1.9 |  | 3.8 |  |
| IPM | 1.1 |  | 1.9 |  | 3.8 |  |
| Carbopol 980 | 0.3 | 0.3 | 0.5 | 0.5 | 1 | 1 |
| water | 97.5 | 99.7 | 95.7 | 99.5 | 91.4 | 99 |
| AMP | q.s to pH = 6 | q.s. to pH = 6 | q.s to pH = 6 | q.s. to pH = 6 | q.s. to pH = 6 | q.s to pH = 6 |
| Viscosity (cp) | 56000 | 46000 | 112000 | 62000 | 183750 | 90000 | q.s. abbreviation means "as much as suffices"
IPM was isopropylmyristate from Alzo.
Carbopol 980 was a carbopol from Lubrizol.
Copolymers 4 is described above.
AMP is aminomethylpropapanol from Dow.

Example 31-33 were prepared by diluting the paste example 27 with a 9.5% solution of aminomethylpropanol (AMP) and water to adjust pH to about 6. Comparative Examples 9, 10 and 11 were prepared by dispersing the carbopol in water and neutralizing the system to pH=6 with aminomethylpropanol.

The hydrophobic polymer and the low polarity diluent fluid (C), isopropylmyristate were mixed together and added to a high molecular weight polydimethylsiloxane (Viscasil 60 M) available from Momentive. Hydrophilic polymer, carbopol Ultrez 20, was dispersed in water at 1% weight concentration

TABLE 4-c

Emulsion composition in wt % prepared from Example 26 (Table 3)

|  | Example 34 | Comparative 12 | Example 35 | Comparative 13 | Example 36 | Comparative 14 |
|---|---|---|---|---|---|---|
| Copolymer 4 | 1.1 |  | 1.9 |  | 3.8 |  |
| IPM | 1.1 |  | 1.9 |  | 3.8 |  |
| Carbopol 1382 | 0.3 | 0.3 | 0.5 | 0.5 | 1 | 1 |
| water | 97.5 | 99.7 | 95.7 | 99.5 | 91.4 | 99 |
| AMP | q.s. to pH = 6 | q.s. to pH = 6 | q.s to pH = 6 | q.s to pH = 6 | q.s to pH = 6 | q.s. to pH = 6 |
| Viscosity (cp) | 60000 | 24500 | 102500 | 34000 | 215500 | 60500 |

IPM was isopropylmyristate from Alzo.
Carbopol 1382 was a carbopol from Lubrizol.
Copolymers 4 is described above.
AMP is aminomethylpropapanol from Dow.

Example 34-36 were prepared by diluting the paste example 26 with a 9.5% solution of aminomethylpropanol (AMP) and water to adjust pH to about 6. Comparative Examples 12, 13 and 14 were prepared by dispersing the carbopol in water and neutralizing the system to pH=6 with aminomethylpropanol.

Example 3

Association Products Formed in Water (Method c)

In this example, hydrophobic polymer was added to the pre-neutralized polyacrylate hydrophilic polymer water gel (Table 6).

and neutralized to pH 6 with aminomethyl propanol from Dow.

In examples 37-42 and 44 of Table 6 the copolymer/isopropylmyrastate/Viscasil 60 M mixture (1 g) was mixed with 2 g of neutralized 1% carbopol Ultrez 20 gel in a 20 ml jar in a Flaktech for 2 min at 2700 rpm. Water was then added slowly to achieve a total final weight of 20 g. In Comparative Example 14, the oil phase comprised 75% Viscasil 60M and 25% isopropylmyristate. All the examples and comparative examples in Table 6 contained 5 wt. % oil phase and 0.1% carbopol Ultrez 20. Viscosity was measured using a Brookfield viscometer at 20 rpm and at a temperature of 25° C. With copolymers 1-7, viscosity of the gel increased with respect to comparative example 14, which does not contain any copolymer. In contrast to the copolymer of the invention, the copolymer in comparative example 15 had a ratio EO/PO in polyether block of 6.5 and significantly decreased the gel viscosity. Similarly the aminosilicone in comparative example 16 that had pendant amino groups also decreased the gel viscosity.

TABLE 5

Polymer A description of example 3

| Hydrophobic Polymer A | Structure | Amine | Polyether (EO) | Polyether (PO) | Ratio EO/PO | Charge of epoxy terminated polysiloxane (g) | Charge of amine (g) |
|---|---|---|---|---|---|---|---|
| copolymer 1 | (iii) | oleylamine | 0 | 0 | NA | 102.86 | 2.00 |
| copolymer 2 | (iii) | oleylamine | 0 | 9 | 0 | 37.5 | 2.2 |
| copolymer 3 | (iii) | oleylamine | 0 | 0 | NA | 100 | 4.73 |
| copolymer 4 | (ii) | ethanolamine | 0 | 0 | NA | 100 | 1.09 |
| copolymer 5 | (iii) | Jeffamine D-4000 | 0 | 66 | 0 | 35.92 | 25.00 |
| copolymer 6 | (iii) | Jeffamine D-2000 | 0 | 33 | 0 | 61.45 | 18.00 |
| copolymer 7 | (iii) | oleylamine | 0 | 9 | 0 | | |
| Comparative 12 | | Silsoft 843 | — | — | 6.5 | — | — |
| Comparative 13 | | Silsoft SF 1708 | | | | | |

The Jeffamines were from Huntsman. Comparative 13 used Silsoft SF1708 which was a commercial grade aminosilicone which has pendant amine groups and no polyether functionality. It is available from Momentive. Comparative 12 used Silsoft 843, which is a copolymer of structure iii, with a EO/PO ratio of about 6.5 and is commercial grade from Momentive.

Preparation Method of Copolymer 1 from Table 5

To a four-necked round-bottomed flask fitted with a mechanical stirrer, a condenser fitted with a nitrogen inlet, a thermocouple and an additional funnel was charged with 102.86 gram of the epoxy-terminated polysiloxane [$CH_2(O)$ $CHCH_2$—O—$(CH_2)_3Si(CH_3)_2[OSi(CH_3))_2]_{380}OSi(Me_2)$ $(CH_2)_3OCH_2CH(O)CH_2$], 2.00 gram of oleylamine, 104.86 g isopropanol, and 100 ppm of Vitamin E. The contents of the flask were heated with stirring to 80° C. until all the epoxy groups were reacted. This typically required 10 hours. The reaction was deemed complete when all the epoxy functionality, determined by titration, was consumed Preparation Method of Copolymer 2 from Table 5

To a four-necked round-bottomed flask fitted with a mechanical stirrer, a condenser fitting with a nitrogen inlet, a thermocouple and an additional funnel, was charged with 37.50 g of the epoxy-terminated polysiloxane [$CH_2(O)$ $CHCH_2O(CH_2)_3Si(CH_3)_2[OSi(CH_3))_2]_{380}OSi(Me_2)(CH_2)_3$ $OCH_2CH(O)CH_2$], 2.20 g of oleylamine, 42.77 g isopropanol, and 100 ppm of Vitamin E. The contents of the flask were heated with stirring to 80° C. for two hours, after which 1.11 g of an epoxy-ended blocked polyalkyleneoxide (DER 732 Commercially available from Dow Chemical) was added to the flask. After two hours of heating, another portion of the epoxy-terminated polysiloxane (37.50 g) was added to the flask. After two hours of heating, 1.11 g of DER 732 was added. The reaction mixture was maintained at 80° C. until all the epoxy groups were reacted. This typically required 10 hours. The reaction was deemed complete when all the epoxy functionality, determined by titration, was consumed.

Preparation Method of Copolymer 3 from Table 5

To a four-necked round-bottomed flask fitted with a mechanical stirrer, a condenser fitted with a nitrogen inlet, a thermocouple and an additional funnel was charged with 100.00 gram of the epoxy-terminated polysiloxane [$CH_2(O)$ $CHCH_2O(CH_2)_3Si(CH_3)_2[OSi(CH_3))_2]_{100}OSi(Me_2)(CH_2)_3$ $OCH_2CH(O)CH_2$], 1.09 gram of oleylamine, 32.19 g isopropanol, and 100 ppm of Vitamin E. The contents of the flask were heated with stirring to 80° C. until all the epoxy groups were reacted. This typically required 10 hours. The reaction was deemed complete when all the epoxy functionality, determined by titration, was consumed.

Preparation Method of Copolymer 4 from Table 5

To a four-necked round-bottomed flask fitted with a mechanical stirrer, a condenser fitted with a nitrogen inlet, a thermocouple and an additional funnel was charged with 100.00 gram of the epoxy-terminated polysiloxane [$CH_2(O)$ $CHCH_2O(CH_2)_3Si(CH_3)_2[OSi(CH_3))_2]_{100}OSi(Me_2)(CH_2)_3$ $OCH_2CH(O)CH_2$], 1.09 gram of ethanolamine, 32.19 g isopropanol, and 100 ppm of Vitamin E. The contents of the flask were heated with stirring to 80° C. until all the epoxy groups were reacted. This typically required 10 hours. The reaction was deemed complete when all the epoxy functionality, determined by titration, was consumed.

Preparation Method of Copolymer 5, 6 from Table 5

The amino-functionalized polymer and a sufficient amount of isopropanol to make a 50% of solution of the final copolymer were charged in a four-neck flask equipped with a stirrer, addition funnel, reflux condenser and thermocouple. The temperature of the reaction mixture was adjusted to 80° C. and an epoxy-terminated polysiloxane: [$CH_2(O)CHCH_2O$ $(CH_2)_3Si(CH_3)_2[OSi(CH_3))_2]_{100}OSi(Me_2)(CH_2)_3OCH_2CH$ $(O)CH_2$] (charges provided in Table 5) was added from an addition funnel. The reaction was completed when the epoxy functionality, determined by titration, was consumed. This typically required 6 to 10 hours.

Preparation Method of Copolymer 7 from Table 5

To a four-necked round-bottomed flask fitted with a mechanical stirrer, a condenser fitting with a nitrogen inlet, a thermocouple and an additional funnel was charged with 37.50 g of the epoxy-terminated polysiloxane: [$CH_2(O)$ $CHCH_2O(CH_2)_3Si(CH_3)_2[OSi(CH_3))_2]_{100}OSi(Me_2)(CH_2)_3$ $OCH_2CH(O)CH_2$], 7.10 g of oleylamine, 61.22 g isopropanol, and 100 ppm of Vitamin E. The contents of the flask were heated with stirring to 80° C. for two hours, after which 3.58 g of an epoxy-ended blocked polyalkyleneoxide (DER 732 Commercially available from Dow Chemical) was added to the flask. After two hours of heating, another portion of the epoxy-terminated polysiloxane (37.50 g) was added to the flask. After two hours of heating, 3.58 g of DER 732 was added. The reaction mixture was maintained at 80° C. until all the epoxy groups were reacted. This typically required 10 hours. The reaction was deemed complete when all the epoxy functionality, determined by titration, was consumed.

The Jeffamines were from Huntsman. Comparative 13 used Silsoft SF1708 which was a commercial grade aminosilicone which has pendant amine groups and no polyether functionality. It is available from Momentive. Comparative 12 used Silsoft 843, which is a copolymer of structure iii, with a EO/PO ratio of about 6.5 and is commercial grade from Momentive.

dispersion and the oil blend were then mixed together with a Flaktech speed mixer for 2 min (method c).

The composition (Comparative 17) that contained a high concentration of polyacrylate thickener (0.95% Carbopol Ultrez 20) and no oil phase (comparative) had very poor

TABLE 6

Composition in wt % and viscosity data

| Hydrophobic Polymer A (from Table 5) | Example 37 | Example 38 | Example 39 | Example 40 | Example 41 | Example 42 | Example 44 | Comparative 14 | Comparative 15 | Comparative 16 |
|---|---|---|---|---|---|---|---|---|---|---|
| copolymer 1 | 1.25 | | | | | | | | | |
| Copolymer 2 | | 1.25 | | | | | | | | |
| Copolymer 3 | | | 1.25 | | | | | | | |
| Copolymer 4 | | | | 1.25 | | | | | | |
| Copolymer 5 | | | | | 1.25 | | | | | |
| Copolymer 6 | | | | | | 1.25 | | | | |
| Copolymer 7 | | | | | | | 1.25 | | | |
| comparative 12 | | | | | | | | | 1.25 | |
| comparative 13 | | | | | | | | | | 1.25 |
| isopropylmyristate | 1.25 | 1.25 | 1.25 | 1.25 | 1.25 | 1.25 | 1.25 | 1.25 | 1.25 | 1.25 |
| carbopol Ultrez 20 | 0.1 | 0.1 | 0.1 | 0.1 | 0.1 | 0.1 | 0.1 | 0.1 | 0.1 | 0.1 |
| Viscasil 60M | 2.5 | 2.5 | 2.5 | 2.5 | 2.5 | 2.5 | 2.5 | 3.75 | 2.5 | 2.5 |
| Water | 94.9 | 94.9 | 94.9 | 94.9 | 94.9 | 94.9 | 94.9 | 94.9 | 94.9 | 94.9 |
| Viscosity (cP) | 7475 | 10250 | 9200 | 9900 | 8200 | 7125 | 7725 | 6600 | 425 | 2475 |

Copolymers 1-7 and Comparative examples 12 and 13 in Table 6 are from the composition of Table 5

Example 4

Hair Gel

Other examples of compositions providing hair conditioning and hair shine and Comparative examples are shown in Table 7.

A 1 wt. % Ultrez 20 carbopol dispersion in water was prepared and neutralized with aminopropyl propanol to pH=6. Separately, the hydrophobic polymer, copolymer 2 from Table 1 and low polarity diluents isopropylmyristate and Viscasil 60M were blended together. The thickened carbopol dispersion and the oil blend were then mixed together with a Flaktech speed mixer for 2 min (method c).

combability (high combing work) and no shine. The addition of isopropylmyristate and Polydimethylsiloxane (Viscasil 60 M) (comparative 18) provided shine, but with only a modest improvement of combability and still a poor feel. The addition of a common O/W emulsifier (Tween 80 from Aldrich) to the isopropylmyristate/Viscasil 60M blend did not improve combing performance (Comparative 19). In contrast, surprisingly, the composition that contained isopropylmyristate, Viscasil 60M and copolymer 2 formed a stable system and provided both high hair shine and very good conditioning (lowest combing work).

TABLE 7

Composition (in wt %) and conditioning performance

| | | Comparative 17 | Comparative 18 | Comparative 19 | Example 45 |
|---|---|---|---|---|---|
| Polymer B | Carbopol Ultrez 20 | 0.95 | 0.95 | 0.95 | 0.95 |
| Diluent C | Isopropylmyristate | | 1.25 | 1.25 | 1.25 |
| | Viscasil 60 M | | 3.75 | 2.5 | 2.5 |
| Polymer A | Copolymer 2 | | | | 1.25 |
| Emulsifier comparative | Tween 80 | | | 1.25 | |
| water | water | 99.05 | 94.05 | 94.05 | 94.05 |
| luster | | low | high | high | high |
| comb Total combing work (mJ) | | 98 | 52 | 49 | 18 |
| Feel | | poor | poor | poor | good/smooth |

*Copolymer 2 is described in Table 1.
Polymer B was a carbopol from Lubrizol and had the trademark Ultrez 20.
Tween 80 was from Aldrich. Viscasil 60 M was a polydimethylsiloxane from Momentive.
Combing force was evaluated in a Diastron combing force apparatus with single bleached tresses.
Luster was evaluated on single bleached hair tresses in a shine box by a hair lab expert, comparing untreated hair and treated hair using (low, medium, high) scale. Feel was evaluated by a hair lab expert on the same tresses.

Example 5

Hair Gel

Other examples of compositions containing low concentrations of hydrophobic polymer and comparative examples are shown Table 8.

The composition with Copolymer 2 was compared to a similar composition where the copolymer 2 was replaced by a conventional emulsifier (Tween 80) and a polymeric emulsifier (Pemulen TR1 from Lubrizol). Emulsions were prepared as in example 3. In example 46 of Table 6 the copolymer/isopropylmyristate/Viscasil 60 M mixture (1.05 g) was mixed with 4 g of neutralized 1% carbopol Ultrez 20 gel in a 20 ml jar in a Flaktech for 2 min at 2700 rpm. Water was then added slowly to achieve a total final weight of 20 g. In Comparative Examples 20-21, the Viscasil 60M/isopropylmyristate mixture (1 g) was blended with the comparative emulsifier (0.05 g) in a Flaktech mixer. This blend was mixed with 4 g of neutralized 1% carbopol Ultrez 20 gel in a 20 ml jar in a Flaktech for 2 min at 2700 rpm. Water was then added slowly to achieve a total final weight of 20 g. Surprisingly, the composition with the copolymer 2 provided the lowest combing work (better conditioning) with a high hair gloss.

TABLE 8

Hair gel composition (in wt %) and conditioning performance

|  |  | Example 46 | Comparative 20 | Comparative 21 |
|---|---|---|---|---|
| Polymer B | carbopol Ultrez 20 | 0.2 | 0.2 | 0.2 |
|  | Viscasil 60 M | 3.75 | 3.75 | 3.75 |
| Diluent C | Isopropylmyristate | 1.25 | 1.25 | 1.25 |
| Polymer A | Copolymer 2 | 0.25 |  |  |
| Comparative emulsifier | Tween 80 |  |  | 0.25 |
| Comparative emulsifier | Pemulen TR1 |  | 0.25 |  |
| water |  | 94.55 | 94.55 | 94.55 |
| luster factor |  | 2.09 | 1.96 | 1.59 |
| Comb Total work (mJ) |  | 33.9 | 44.9 | 46.2 |
| Feel |  | soft | poor | poor |

Copolymer 2 is described in Table 1.
Polymer B was a carbopol from Lubrizol and had the trademark Ultrez 20.
Tween 80 was from Aldrich.
Pemulen TR1 is a acrylate based polymeric emulsifier from Lubrizol.
Viscasil 60 M is a polydimethylsiloxane from Momentive.

A fixed dose of the compositions shown was spread on single bleached (0.2 g/g of hair) and dried with a blow drier. Hair luster was measured with a Murakami spectrogoniophotometer. The hair reflectance was measured using a fixed incident angle of 35° and a viewing angle varying from 0° to 80°. The luster factor G was calculated using the reflectance value D obtained at 0° viewing angle and the maximum value of reflectance S, G=(S−D)/D. Total combing work was measured on single bleached tresses with a Diastron combing force apparatus.

Example 6

Hair Gel

Composition example 47 and Comparative Examples 22-23 are shown table 9. The components (A) and (C) were first blended together. They were added to the thickener Sepigel 305. Then water was added slowly to the mix, until final composition was reached.

A fixed dose of the compositions shown was spread on single bleached (0.2 g/g of hair) and dried with a blow drier. Hair luster was measured with a Murakami spectrogoniophotometer. The hair reflectance was measured using a fixed incident angle of 35° and a viewing angle varying from 0° to 80°. The luster factor G was calculated using the reflectance value D obtained at 0° viewing angle and the maximum value of reflectance S, G=(S−D)/D. Total combing work was measured on single bleached tresses with a Diastron combing force apparatus.

Data showed that the composition containing the polyacrylamide polymeric thickened gel and a low polarity organic oil (comparative 22) spread and dried on the hair inferred very poor combability and feel to the hair, with no shine enhancement. Addition of PDMS (comparative 23) provided shine, but with only a modest improvement of combability and still a poor feel. In contrast, surprisingly, example 47 containing Sepigel 305, isopropylmyristate, Viscasil 60 M and copolymer 2 formed a stable system providing both high hair shine with very good conditioning (lowest combing force).

TABLE 9

|  |  | comparative 22 | comparative 23 | Example 47 |
|---|---|---|---|---|
| Polymer B | Sepigel 305 | 1 | 1 | 1 |
| Diluent C | Isopropylmyristate | 5 | 1.25 | 1.25 |
| Diluent C | Viscasil 60 M |  | 3.75 | 2.5 |
| Polymer A | copolymer 2 |  |  | 1.25 |
|  | water | 94 | 94 | 94 |
|  | luster factor | 1.09 | 1.65 | 1.65 |
|  | Total combing force (mJ) | 60.7 | 39.0 | 25.4 |
|  | subjective evaluation | no shine | shine | shine |
|  | feel | poor feel | poor feel | soft feel |
|  | Emulsion stability | stable | stable | stable |

*Sepigel 305 was a polyacrylamide based thickener from Seppic (Inci name: polyacrylamide and C13-C14 isoparaffin and laureth-7) Copolymer 2 is described in Table 1.
Viscasil 60 M was a polydimethylsiloxane from Momentive

Example 7

Hair Care Emulsion Composition in Wt %

TABLE 10

| Polymer B | Xanthan gum | 1 | 1 |
|---|---|---|---|
| Diluent C | isopropylmyristate | 1.25 | 1.25 |
| Diluent C | Viscasil 60 M | 2.5 | 3.75 |
| Polymer A | Copolymer 2 | 1.25 |  |
|  | Water | 94 | 94 |
| Luster factor |  | 2 | 1.9 |
| Feel |  | smooth | poor |

Xanthan gum, isopropylmyristate, Viscasil 60 M and copolymer 2 (from table 1) were blended together at room temperature with a Flaktech speedmixer. Water was added to this blend and mixed with a Flaktech speedmixer. For the comparative, Xanthan gum, isopropylmyristate, Viscasil 60 M were blended together at room temperature with a Flaktech speedmixer. Water was added and mixed with a Flaktech speedmixer. A fixed dose of the compositions shown was spread on single bleached (0.2 g/g of hair) and dried with a blow drier. Hair luster was measured with a Murakami spectrogoniophotometer. The hair care emulsion with copolymer 2 provided both a smooth feel and a high hair luster.

Xanthan gum was from Cargill and had the tradename Satiaxane CX800. Copolymer 2 is described in Table 1.

What is claimed is:

1. A composition comprising a non-covalent bonded reaction product of (A) a hydrophilic polymer containing an acid functional group and (B) a hydrophobic polymer which contains an amine group bound directly to the hydrophobic polymer backbone and which either does not contain an ethylene oxide moiety or contains an ethylene oxide moiety to propylene oxide moiety in a ratio of less than 3, wherein the non-covalent bonded reaction product is prepared by method (a) which comprises (a-i) blending hydrophilic polymer (A) and hydrophobic polymer (B) in a molar ratio of amine:acid from 0.01:1 to 1:1 in a non-aqueous medium at the temperature in the range of 30° C. to 200° C. for a period of from about 1 minute to about 120 minutes to produce a blend, and (a-ii) cooling the blend obtained from step (a-i) to room temperature to provide the non-covalent bonded reaction product; or method (b) which comprises (b-i) blending hydrophilic polymer (A) and hydrophobic polymer (B) in a molar ratio of amine:acid from 0.01:1 to 0.2:1 in a non-aqueous medium at the temperature in the range of 30° C. to 200° C. for a period of from about 1 minute to about 120 minutes to produce a blend, (b-ii) adding an aqueous base solution to the blend obtained from step (b-i) at the temperature in the range of 30° C. to 95° C. to produce a mixture, and (b-iii) cooling the mixture obtained from step (b-ii) to room temperature to provide the non-covalent bonded reaction product;

wherein the hydrophobic polymer which contains an amine group bound directly to the hydrophobic polymer backbone is an amino silicone copolymer with a (ABA) structure where B is the siloxane block, resulting from the reaction of:

$R^1R^2NH$ where $R^1=R^3(OC_aH_{2a})_m$— and where $R^3=(C_nH_{2n+1})$— and where n is an integer of from 1 to 30, or where $R^3=(C_nH_{2n-1})$— where n is an integer of from 2 to 30, or where $R^3=(C_nH_{2n-3})$— where n is an integer of from 4 to about 30, and m=0 or an integer of from 1 to 200, and a is an integer of from 2 to 4, where $R^2=H$ or $R^4(OC_cH_{2c})_o$— where $R^4=(C_qH_{2q+1})$— where q is an integer of from 1 to 30, or where $R^4=(C_qH_{2q-1})$— where q is an integer of from 2 to about 30, or where $R^4=(C_qH_{2q-3})$— where q is an integer of from 4 to 30, and o=0 or an integer of from 1 to 200 and, c is an integer of from 2 to 4; and

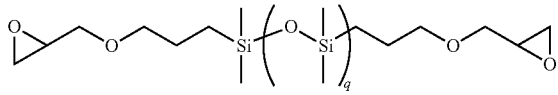

wherein q is an integer of from 2 to 1000.

2. The composition of claim 1 wherein acid functional group of the hydrophilic polymer is at least one of a carboxylic group, a sulfonic group and a phosphonic group.

3. The composition of claim 1 wherein the hydrophilic polymer containing an acid functional group is selected from the group consisting of:
(I) polyacrylates polymers;
(II) homopolymers containing monomers containing sulfonic groups;
(III) copolymers containing monomers containing sulfonic groups; and
(IV) polysaccharides containing acidic groups.

4. The composition of claim 1 wherein the hydrophilic polymer containing an acid functional group and a hydrophobic polymer which contains an amine group bound directly to the hydrophobic polymer backbone are present in an amount such that there is an amine/acid ratio of from about 1:20 to about 1:1.

5. The composition of claim 1 wherein the composition is other than a fabric treatment composition.

6. The composition of claim 1 wherein the non-covalent bonded reaction product comprises at least one hydrogen bond or at least one ionic bond.

7. An aqueous emulsion comprising the composition of claim 1.

8. A composition selected from the group consisting of a personal care composition, a cosmetic composition, a textile composition, an oil extraction composition, a coating composition, a paint composition, an agriculture composition, a lubrication composition, a composition requiring irreversible thickening, and an emulsification composition, wherein the composition comprises the composition of claim 1.

9. A personal care composition comprising the composition of claim 1.

10. A hair care or skin care composition comprising the composition of claim 1.

11. The composition of claim 1 wherein the subscript q in

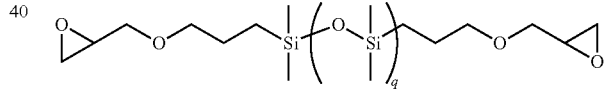

is an integer of from 10 to 500.

12. A process of making a composition comprising non-covalently reacting a hydrophilic polymer containing an acid functional group and; a hydrophobic polymer which contains an amine group bound directly to the hydrophobic polymer backbone and which either contains no ethylene oxide moieties or contains an ethylene oxide moiety to propylene oxide moiety ratio of less than 3 wherein the non-covalent bonded reaction product is prepared by method (a) which comprises (a-i) blending hydrophilic polymer (A) and hydrophobic polymer (B) in a molar ratio of amine:acid from 0.01:1 to 1:1 in a non-aqueous medium at the temperature in the range of 30° C. to 200° C. for a period of from about 1 minute to about 120 minutes to produce a blend, and (a-ii) cooling the blend obtained from step (a-i) to room temperature to provide the non-covalent bonded reaction product; or method (b) which comprises (b-i) blending hydrophilic polymer (A) and hydrophobic polymer (B) in a molar ratio of amine:acid from 0.01:1 to 0.2:1 in a non-aqueous medium at the temperature in the range of 30° C. to 200° C. for a period of from about 1 minute to about 120 minutes to produce a blend, (b-ii) adding an aqueous base solution to the blend obtained from step (b-i) at the temperature in the range of 30° C. to 95° C. to produce a mixture, and (b-iii) cooling the mixture obtained from step (b-ii) to room temperature to provide the non-covalent bonded reaction product.

* * * * *